United States Patent [19]

Korach

[11] 4,318,698
[45] Mar. 9, 1982

[54] DEVICE FOR STABILIZING A TOOTH AND A METHOD FOR ITS USE

[76] Inventor: Haim Korach, 11 Epstein Rd., Tel-Aviv, Israel

[21] Appl. No.: 113,962

[22] Filed: Jan. 21, 1980

[30] Foreign Application Priority Data

Jun. 14, 1979 [IL] Israel ........................ 57566

[51] Int. Cl.³ .................................. A61C 5/04
[52] U.S. Cl. ........................................ 433/225
[58] Field of Search .............. 433/226, 225; 411/337, 411/366

[56] References Cited

U.S. PATENT DOCUMENTS

| | | | |
|---|---|---|---|
| 877,061 | 1/1908 | Earnest | 411/338 |
| 1,416,558 | 5/1922 | Holtz | 433/225 |
| 1,616,232 | 2/1927 | Roberts et al. | 411/338 |
| 3,576,073 | 4/1971 | Weissman | 433/225 |

Primary Examiner—Robert Peshock
Attorney, Agent, or Firm—Birch, Stewart, Kolasch & Birch

[57] ABSTRACT

The present invention relates to a device for the stabilization of teeth, in particular molar teeth having a cavity which comprises a screw provided with an outer thread and means at its outer end for holding it and a hollow nut provided with an inner thread adapted to the outer thread of the screw and means at the outer end of the nut for holding it. The present invention also relates to a method for the treatment of a tooth having a cavity with the aid of said device.

6 Claims, 3 Drawing Figures

DEVICE FOR STABILIZING A TOOTH AND A METHOD FOR ITS USE

BACKGROUND OF THE INVENTION

The present invention relates to a device for stabilizing a tooth in particular a molar or pre-molar tooth (hereinafter called "molar tooth") having a cavity and to a method for the application of said device.

In teeth, particularly in molar teeth, sometimes a cavity has to be formed in the course of treatment of said teeth. It is quite complicated to stabilize said teeth and to treat same. (Up to now such a tooth was treated by means of building a crown on it).

There are certain known devices and methods for similar purposes, e.g., those described in U.S. Pat. Nos. 3,590,486, 3,813,778, 3,831,281 and 3,874,081. However, said devices and methods are not applicable for the present purpose.

It has hence been desirable to design a device for the stabilization of a tooth having a cavity and to find a method for the application of said device.

SUMMARY OF THE INVENTION

The present invention thus consists in a device for the stabilization of teeth, in particular molar teeth (as herein defined) having a cavity, which comprises a screw provided with an outer thread and means at its outer end for holding it and a hollow nut provided with an inner thread adapted to the outer thread of the screw and means at the outer end of the nut for holding it.

The device according to the present invention may be applied to teeth where the outer walls are intact and the cavity is between same.

The length of the assembled device is substantially the width of the tooth. (The width of the tooth in connection with the present invention means the distance of the outside of the walls of the tooth from the inside to the outside of the mouth).

In a preferred embodiment of the device according to the present invention the screw is not entirely cylindrical but has two partially flat outer surfaces. Moreover, advantageously the nut has a tongue-like extension which enables a tight locking operation after insertion of the device and addition of the dental filler.

The device according to the present invention may be made of any suitable material, preferably stainless steel which is advantageously silver or gold plated.

The invention thus consists also in a method for the treatment of a tooth having a cavity with the aid of the above device in which a hole is bored in both walls of the tooth the diameter of which corresponds substantially to that of the screw, then spot faces are prepared on the outer surfaces of the walls, thereafter the screw from the one side and the nut from the other side are inserted and screwed to each other and thereafter a dental filling is added to fill the cavity of the tooth.

Preferably before the screw and the nut are inserted, the spot faces and the bores (holes) are etched and thereafter a suitable resin-bonded crystalline silicon dioxide composition is applied to said spot faces and holes.

Advantageously, the outer parts of said devices are coated with some suitable material, e.g., plastic.

Sometimes the screw is too long and can then be cut outside the tooth after it has passed through the nut.

BRIEF DESCRIPTION OF THE DRAWINGS

The present invention will now be illustrated with reference to the accompanying drawings without being limited by them. Identical parts are marked by the same reference numerals. In said drawings.

DETAILED DESCRIPTION OF THE INVENTION

Figures 2, 3:
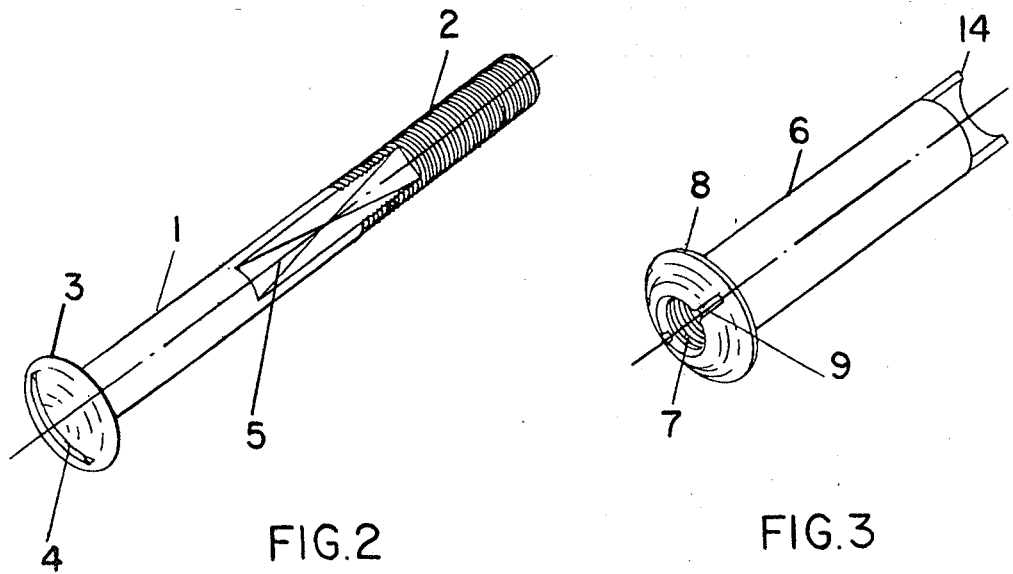
FIG. 2 shows a screw of the device according to the present invention.
FIG. 3 shows a nut of a device according to the present invention.
Figure 1:
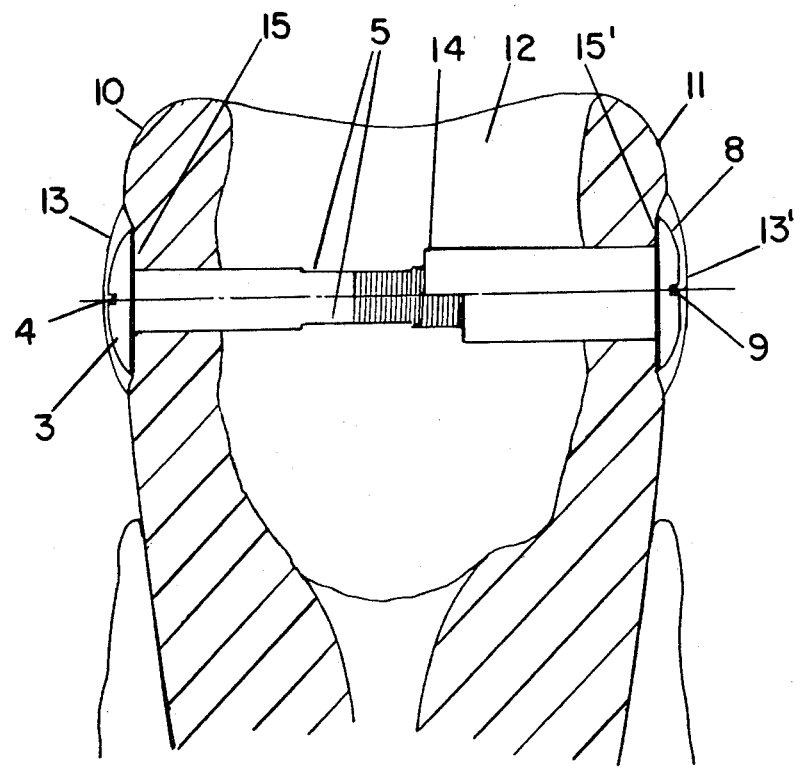
FIG. 1 shows a device according to the present invention fixed inside a molar tooth.

The screw illustrated in FIGS. 1 and 2 comprises body 1 on which is arranged thread 2. At its end is arranged head 3 with holding groove 4. On both sides of body 2 are arranged flat surfaces 5.

The nut illustrated in FIGS. 1 and 3 comprises hollow body 6 with inner thread 7. At its end is arranged head 8 with holding groove 9 and being provided with tongue like extension 14.

When the device is to be applied to the tooth holes (not shown) are bored through walls 10 and 11 and spot faces 15 and 15' are prepared.

Advantageously a suitable resin-bonded silicon dioxide composition, e.g., such as prepared by Healthco Inc., Boston, is applied to spot faces 15 and 15' and to the holes (not shown).

Then the screw and the nut are passed through said holes each through a different wall, screwed together by holding screw drivers in grooves 4 and 9. Thereafter the dental filling is put into cavity 12.

If desired heads 4 and 9 may be coated with layers 13 and 13', respectively.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A device for the stabilization of a tooth, in particular a molar tooth, having a cavity, which comprises a screw provided with an outer thread on one end thereof and a means at its end opposite said thread for holding said screw and a hollow nut provided with an inner thread at one end adapted to fit the outer thread of said screw and a means at the opposite end thereof for holding said nut, said nut having a tongue-like extension at the thread end thereof which enhances the locking effect of said nut, and said screw having two partially flat outer surfaces which further enhance the mechanical locking of said device.

2. A device according to claim 1 which is made of stainless steel.

3. A device according to claim 1 wherein said means for holding each of said screw and nut comprises a head and a holding grove.

4. A method for the treatment of a tooth having a cavity which comprises providing a tooth stabilizing device comprising a screw provided with an outer thread on one end thereof and means at its end opposite said thread for holding said screw and a hollow nut provided with an inner thread at one end adapted to fit the outer thread of said screw and a means at the opposite end thereof for holding said nut, boring a hole in both walls of the respective tooth, the diameter of which corresponds substantially to that of said screw, preparing spot faces at the outer surfaces of the walls of the tooth where said holes are bored, inserting said screw from one side and said nut from the other side of said tooth, screwing one to the other and thereafter adding a dental filling to fill the cavity of the tooth.

5. A method according to claim 4, wherein a resin-bonded crystalline silicon dioxide composition is applied to said spot faces and hole prior to the insertion of said screw and nut.

6. A method according to claim 4, in which the outer parts of said device are coated.

* * * * *